(12) United States Patent
de la Torre et al.

(10) Patent No.: US 11,710,554 B2
(45) Date of Patent: Jul. 25, 2023

(54) METHOD FOR DIAGNOSIS AND DOCUMENTATION OF HEALTHCARE INFORMATION

(71) Applicant: Steward Health Care System LLC, Boston, MA (US)

(72) Inventors: Ralph de la Torre, Boston, MA (US); Justine M. Carr, Chestnut Hill, MA (US)

(73) Assignee: Steward Health Care System LLC, Boston, MA (US)

( * ) Notice: Subject to any disclaimer, the term of this patent is extended or adjusted under 35 U.S.C. 154(b) by 1364 days.

(21) Appl. No.: 14/670,172

(22) Filed: Mar. 26, 2015

(65) Prior Publication Data

US 2015/0278457 A1 Oct. 1, 2015

Related U.S. Application Data

(60) Provisional application No. 61/970,655, filed on Mar. 26, 2014.

(51) Int. Cl.
*G16H 40/20* (2018.01)
*G16H 50/20* (2018.01)
*G16H 15/00* (2018.01)

(52) U.S. Cl.
CPC .......... *G16H 40/20* (2018.01); *G16H 15/00* (2018.01); *G16H 50/20* (2018.01)

(58) Field of Classification Search
CPC .... G06F 19/325; G06F 19/345; G06F 19/327; G06F 19/328; G16H 50/20; G16H 40/20; G16H 15/00
See application file for complete search history.

(56) References Cited

U.S. PATENT DOCUMENTS

| 5,018,067 | A  | * | 5/1991 | Mohlenbrock | ....... | G06F 19/328 128/920 |
| 8,090,621 | B1 | * | 1/2012 | Chakrabarti | ....... | G06Q 30/0601 705/26.1 |
| 2005/0065817 | A1 | * | 3/2005 | Mihai | ..................... | A61B 5/411 705/2 |
| 2007/0165790 | A1 | * | 7/2007 | Taori | .................. | H04M 3/5307 379/67.1 |

(Continued)

*Primary Examiner* — Gregory D. Moseley
(74) *Attorney, Agent, or Firm* — Locke Lord LLP; Christopher J. Capelli

(57) ABSTRACT

A method for developing codes and a cross functional set of rules that suggest to a physician, in real-time, potential diagnoses related to diagnostic results or other clinical data entered into the electronic Medical Record (EMR). The method generates a possible diagnosis for consideration and addition to the patient problem list. When the physician selects a suggested diagnosis, the problem list is automatically updated with the diagnosis. In view of the above, the physician has the needed information at the point of care so that the timeliness, safety and quality of care is improved. The generated documentation also assists other physicians throughout the continuum of care for the Patient. The method creates crosswalk from data element to diagnosis to enhance the completeness of documentation. As a result, the Diagnostic Related Group (DRG) is more accurately assigned by coders at discharge to drive more accurate and efficient billing for improved reimbursement and revenue.

7 Claims, 12 Drawing Sheets

(56) References Cited

U.S. PATENT DOCUMENTS

| | | | |
|---|---|---|---|
| 2008/0086327 A1* | 4/2008 | Cox | G06Q 10/00 |
| | | | 705/2 |
| 2008/0133275 A1* | 6/2008 | Haug | G06Q 10/06 |
| | | | 705/3 |
| 2008/0281638 A1* | 11/2008 | Weatherly | G16H 50/30 |
| | | | 705/3 |
| 2008/0287746 A1* | 11/2008 | Reisman | G16H 50/20 |
| | | | 600/300 |
| 2010/0191546 A1* | 7/2010 | Kanamarlapudi | G16H 10/60 |
| | | | 705/3 |
| 2010/0223073 A1* | 9/2010 | Nearman | G16H 80/00 |
| | | | 705/3 |
| 2011/0202370 A1* | 8/2011 | Green, III | G06F 19/328 |
| | | | 705/3 |
| 2013/0179178 A1* | 7/2013 | Vemireddy | G06Q 10/00 |
| | | | 705/2 |
| 2013/0278414 A1* | 10/2013 | Sprigg | G08B 21/0453 |
| | | | 340/539.12 |
| 2014/0047375 A1* | 2/2014 | Koll | G06F 3/0481 |
| | | | 715/780 |
| 2014/0067424 A1* | 3/2014 | Ramakrishnan | G06F 19/328 |
| | | | 705/3 |

* cited by examiner

| CODE | DESCRIPTION | CLINICAL TRIGGERS | KEEP ON DISCHARGE | HIS CODE | PROBLEM PRIORITY IN HIS | PROBLEM STATUS IN HIS | DO NOT TRIGGER IF THESE Dx ARE ON THE PROBLEM LIST | BUNDLED WITH |
|---|---|---|---|---|---|---|---|---|
| 276.1 | HYPOSMOLALITY AND/OR HYPONATREMIA | SODIUM<130 | NO | 89627008 | HIGH | ACTIVE | 276.1 | 250.12, 250.13, 25.20 |
| 276.2 | ACIDOSIS | pH<=7.35 | NO | 51387008 | HIGH | ACTIVE | 276.2 | 250.12, 250.13, 25.20 |
| 276.3 | ALKALOSIS | pH<=7.47 | NO | S.CMALKALOSIS | HIGH | ACTIVE | 276.3 | 250.12, 250.13, 25.20 |
| 284.2 | PANCYTOPENIA | HCT<30 AND WBC <4 AND PLATELETS <100 | NO | 127034005 | HIGH | ACTIVE | 284.19 | 518.81, 518.83 518.84 |
| 276 | HYPEROSMOLALITY AND/OR HYPERNATREMIA | SODIUM>150 | NO | 39355002 | HIGH | ACTIVE | 276 | 518.81, 518.83 518.84 |
| 410.9 | AMI NOS, INITIAL | TROPONIN>10 | NO | S.CMMI | HIGH | ACTIVE | 410.91, 411.89 | 518.81, 518.83 518.84 |
| 570 | ACUTE NECROSIS OF LIVER | ALT>1000 AND AST>1000 | NO | 37871000 | HIGH | ACTIVE | 570 | |
| 286.6 | DEFIBRINATION SYNDROME | FIBRINOGEN<100 | YES | S.CMDEFIBRIN | HIGH | ACTIVE | 286.6, 571.5 | |
| 588.8 | SEC HYPERPARATHYRD-RENAL | PTH>55pg/mL AND GFR<15 | NO | 19034001 | HIGH | ACTIVE | 588.81 | |
| 568.8 | HEMOPERITONEUM | PERITONEAL FLUID rbc:>500- IGNORE LABS COMING AS "1000" AND "<3000" | NO | S.HEMOPERITONE U | HIGH | ACTIVE | 568.81 | |

FIG. 8

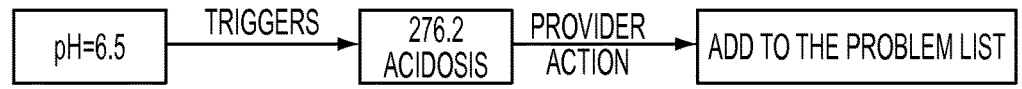
ANY TIME AFTER THE ADDITION TO THE PROBLEM LIST
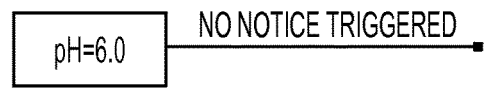
ANY TIME AFTER THE ADDITION TO THE PROBLEM LIST
REGARDLESS OF THE TIMING OF THE NEXT LAB THAT MATCHES THE CLINICAL TRIGGERS
pH=6.0    NO NOTICE TRIGGERED
FIG. 10

ANY TIME AFTER THE FIRST NOTICE HAS BEEN FLAGGED AS DO NOT ADD WITH
REASON = "INSUFFICIENT DATA" OR "UNRELIABLE SPECIMEN"

REGARDLESS OF THE TIMING OF THE NEXT LAB THAT MATCHES THE CLINICAL TRIGGERS pH=6.0 —— NO NOTICE TRIGGERED

---

30 MINUTES AFTER THE FIRST LAB MESSAGE IS RECEIVED BY THE RULES ENGINE

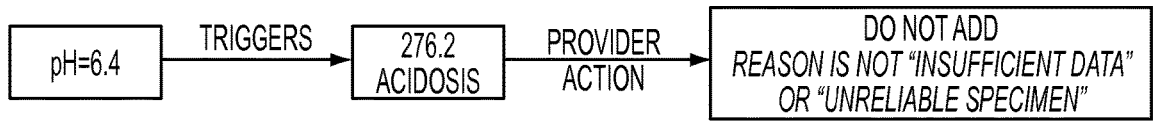

ANY TIME AFTER THE SECOND NOTICE WAS FLAGGED AS DO NOT ADD WITH REASON <> INSUFFICIENT DATA

---

30 MINUTES AFTER THE FIRST LAB MESSAGE IS RECEIVED BY THE RULES ENGINE

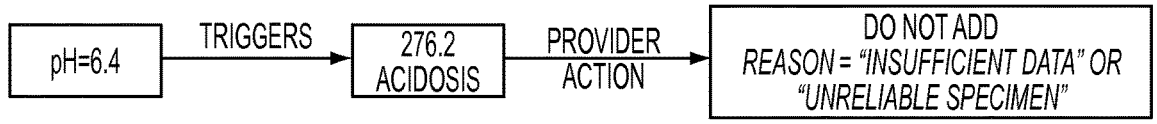

30 MINUTES AFTER THE SECOND LAB MESSAGE IS RECEIVED BY THE RULES ENGINE

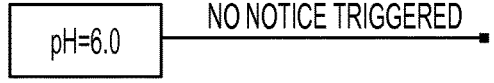

FIG. 12

METHOD FOR DIAGNOSIS AND DOCUMENTATION OF HEALTHCARE INFORMATION

CROSS-REFERENCE TO RELATED APPLICATION

This application claims the benefit of and priority to U.S. Provisional Patent Application No. 61/970,655, filed Mar. 26, 2014, which is incorporated herein by reference.

BACKGROUND OF THE TECHNOLOGY

1. Field of the Technology

The present technology relates to healthcare management and, more particularly, methods and systems designed specifically to manage healthcare workflow such as in co-morbidity situations, determine various events related to same, and provide tools that analyze the paper trail to produce results.

2. Description of the Related Art

As a person seeks medical care, the person interacts with a health care system. The interaction and progression through the health care system is known as a patient trajectory. At each step along the patient trajectory, a paper trail is created known as the medical record. This medical record is critical to assist caregivers with diagnosis and treatment as well as establish the basis for payment.

To assist with creation of accurate medical records, a system of classification of diseases has been developed. These classification systems play a ubiquitous and important role in providing and administering healthcare. A classification system called the International Classification of Diseases (ICD) has been developed and widely adopted as the preferred classification system in health care. Currently, the ninth version of ICD (ICD-9) is commonly used but soon a tenth version will be implemented (ICD-10). ICD-10 will have thousands of codes.

Still other classification systems, such as diagnosis-related groups (DRGs) are based on ICD codes for Medicare and other reimbursement purposes. DRGs were designed to be homogeneous units of hospital activity to which binding prices could be attached. DRGs were intended to describe all types of patients in an acute hospital setting. The DRGs encompassed elderly patients as well as newborn, pediatric and adult populations.

As would be appreciated, the initial paper trail begins with admission and proceeds to having clinicians and other caregivers record observations, tests, procedures and the like. As this diagnostic process may progress across different providers, the efficient flow of information can be derailed by missteps as simple as illegible handwriting, incompatible hardware systems, inconsistent term usage and the like. Yet somehow, the medical record must accurately contain the steps taken and ultimate diagnosis. Typically, a health information department assists the clinicians, caregivers, and service providers with compiling the patient medical record. The medical records are then transcribed to create a final medical record for review by a medical coding specialist.

Medical coding specialists or coders are responsible for correctly assigning diagnostic codes to healthcare claims in order to obtain reimbursement from insurance companies and government healthcare programs, such as Medicare. Medical coders work in the billing office, or "back office" of medical practices and hospitals. Medical coders help to complete, review, and process medical claims to help physician practices and hospitals get reimbursed from insurance companies for services and resources provided to patients. In short, medical coders assign DRGs based on the ICDs in the medical record. Accurate DRG assignment drives accurate and efficient billing for complete reimbursement and revenue. At times, if the medical record is unclear, the coder may have to obtain additional information from a physician or other medical provider.

As can be seen, the coding process is replete with opportunity for information to be misinterpreted or even missing. A common example of errors occurring is when co-morbidity is present. Co-morbidity is the presence of a morbid condition, disease or disorder in a patient in addition to the condition for which the patient was initially admitted. Assessment is when patient data indicates the possible presence of a co-morbidity. Co-morbidity carries considerable weight in the assignment of the DRG classification of diseases which in turn identifies the expected length of hospitalization. Co-morbidity also impacts the severity risk assessment of outcomes.

Accurate capture of comorbidities is important to the clinical care of the patient as well as to the revenue from payers. Several challenges exist in traditional capture of co-morbidities. One challenge is that only documentation by a physician, nurse practitioner or physician assistant may be used for coding. In addition, a physician's description may be sufficient for clinical documentation, but may not meet criteria required medical record coders to code. Another challenge is that co-morbid conditions need to be recognized and communicated in a timely fashion to current and future care providers. With the emergence of an electronic medical record (EMR) for every patient, the "Problem List" has emerged as a quick synopsis of key issues . . . . Adoption of the Problem List has been variable among physicians. However, a Problem List is an excellent source of documentation source for the coders because the diagnoses that appear are documented by the physicians and thus usable for coding. Use of the Problem List is also important for hospitals to receive for federal Meaningful Use incentive payments.

SUMMARY OF THE TECHNOLOGY

In view of the above, a need exists for systems and method that effectively analyzes the electronic Medical Record (EMR) in real-time to assist clinicians at the point of care to improve the timeliness, safety and quality of the care. The improved methods and systems would also enhance the accuracy of the EMR to drive more accurate and efficient reimbursement.

The present disclosure relates to methods of healthcare management and systems particularly designed to accomplish such methods. For example, the present technology has a rules-based interface between clinical diagnosis and co-morbidity assessment, where a co-morbidities assessment rules engine evaluates real-time patient data for potential diagnoses (e.g., laboratory results, body-mass index (BMI), etc.). The co-morbidity assessment rules engine may be provided in a device that receives input (e.g., data, parameters related to events, and even raw test material) for analysis, evaluation and determination of results that may be presented in a variety of forms including tactile, paper, digital, and other visual forms.

If the condition suggested by the data is not already on a Problem List, co-morbidity alerts may then be immediately broadcasted to the next or all licensed independent practitioners (LIPs) (e.g., physician, nurse practitioner, or physician assistant) who access the patient's hospital record. The LIPs must take an action either to add the problem to the Problem List or decline. Alerts continue to LIPs until an action is taken. When the problem is added, the net benefit is that the immediate care providers are alerted and future care providers will also be alerted. The problem is captured in language that can be used by the medical record coders and under the signature of the LIP and the Problem List meets criteria for Meaningful Use incentive payment. Also, the subject technology further provides a device interface between patient diagnosis data, lab requests, billing codes and the like.

Preferably, the rules engine device can suggest the provider add a problem to the patient's Problem List. The rules engine device takes patient data and observations, evaluates a list of rules for possible matches, and then creates and sends notices of potential problems to be displayed to the healthcare provider. The rules engine device will alert physicians when additional undiagnosed problem may exist for a patient. This functionality is made possible through an interface and a rules engine where physicians will be notified of high probability diagnosis codes that can be added on their Problem List. When alerted, physicians will then be able to easily add the missing diagnosis codes to the patient's record. The techniques herein, therefore, significantly improve patient care and increase reimbursement by implementing a new workflow to maximize physician co-morbidity coding.

It should be appreciated that the subject technology can be implemented and utilized in numerous ways, including without limitation as a process, an apparatus, a system, a device, a method for applications now known and later developed or a computer readable medium. These and other unique features of the methods and systems disclosed herein will become more readily apparent from the following description and the accompanying drawings.

BRIEF DESCRIPTION OF THE DRAWINGS

So that those having ordinary skill in the art to which the disclosed methods and systems appertain will more readily understand how to make and use the same, reference may be had to the following drawings.

FIG. 8 is a table of a subset of rules and their corresponding entry values in accordance with an embodiment of the present technology.

FIGS. 10-12 is various examples of notice triggering according to the subject technology.

DETAILED DESCRIPTION OF THE TECHNOLOGY

Figure 1:
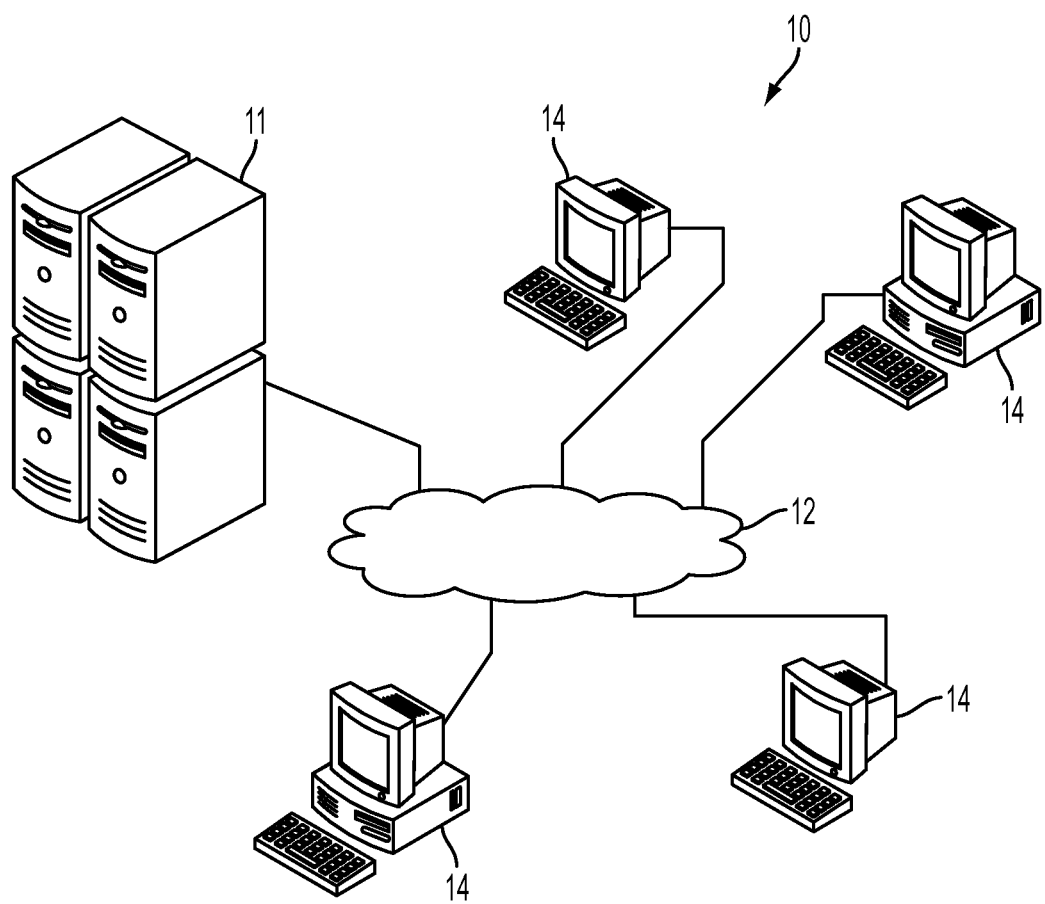
FIG. 1 is a diagram showing a distributed computing environment for utilizing methods for managing co-morbidity in accordance with the subject disclosure.

The subject technology overcomes many of the prior art problems associated with methods, systems and devices for providing and administering medical care, and particularly in treating co-morbidity in a reliable manner. The advantages, and other features of the methods, systems and devices disclosed herein, will become more readily apparent to those having ordinary skill in the art from the following detailed description of certain preferred embodiments taken in conjunction with the drawings which set forth representative embodiments of the present technology and wherein like reference numerals identify similar structural elements.

Although the following examples are with respect to co-morbidity, it will be appreciated that the present technology is applicable to a wide array of scenarios. In brief overview, the present technology provides systems, methods and devices that evaluate patient data (the EMR) for potential co-morbidities after each clinical. A clinical may be a lab, BMI, medical order, radiology report, and the like. Alerts are selectively broadcast to targeted users in their existing workflows.

As noted above, co-morbidity is the simultaneous presence of two or more morbid conditions or diseases in the same patient, which may complicate a hospital stay. Co-morbidity carries considerable weight in determining the reasonable length of hospitalization under the DRG classification of diseases. Unfortunately, not all eligible comorbidity codes are being associated to patient visits, which results in patient safety issues and loss of reimbursement. The present technology employs a rules engine that reviews the EMR and updates the "Problem List."

Referring now to the FIG. 1, there is shown a block diagram of an environment 10 that may embody and implement the methodology of the present disclosure. The following discussion describes the structure of such an environment 10 but further discussion of the applications programs and data that embody the methodology of the present technology is described elsewhere herein. The present technology allows users, who generate and/or gather data for healthcare information, such as electronic Medical Records (EMR), to enter data. The users may be clinicians or other caregivers, medical professionals, staff, medical coders and the like.

The environment 10 includes one or more servers 11 which communicate with a distributed computer network 12 via communication channels, whether wired or wireless, as is well known to those of ordinary skill in the pertinent art. In a preferred embodiment, the distributed computer network 12 is the Internet. For simplicity, although a plurality of servers 11 are shown, the term server 11 applies well to the grouping as such computing power is well-known to be aggregated. Server 11 hosts multiple Web sites and houses multiple databases necessary for the proper operation of the central monitoring methods in accordance with the subject technology.

The server 11 is any of a number of servers known to those skilled in the art that are intended to be operably connected to a network so as to operably link to a plurality of clients or user computers 14 via the distributed computer network 12. The plurality of computers or clients 14 may be desktop computers, laptop computers, personal digital assistants, tablet computers, scanner devices, cellular telephones and the like. The clients 14 allow users to enter and access information on the server 11. For simplicity, only four clients 14, 16 are shown but the number and location are unlimited. The clients 14 have displays and an input device(s) as would be appreciated by those of ordinary skill in the pertinent art.

It is understood that each of the devices 11, 14 of the environment 10 include a processor, memory storing executable code and other interconnected hardware to accomplish the functions and goals of the subject technology. Additionally, the hardware and software of the devices 11, 14 can be particularly configured and programmed to be particularly suitable for the purposes of the subject technology. For example in the environment 10, the servers 11 would store rules and program modules that can employ other rules (e.g., a business rules engine and its components). The servers 11 would also receive, store and send the necessary information including, without limitation, a rules database, clinical triggers, co-morbidity indicators, an alert manager module, an encounter manager module, and like.

The environment 10 also provides for administration and security maintenance. Therefore, although each user (e.g., data managers, medical conders, caregivers, clinicians, nurses, staff etc.) of the subject technology has access to a user interface on a client 14, each group's access is controlled. The interface specifies which aspects of the program can be accessed, and at what level in order to maintain compliance with technical electronic data interchange standards and legal confidentiality restraints such as HIPAA (Health Insurance Portability and Accountability Act) and quality standards such as GCP (Good Clinical Practice). Such limitations of functionality are well known to those skilled in the art and therefore not further described herein.

The flow charts herein illustrate the structure or the logic of the present technology, possibly as embodied in computer program software for execution on a computer, digital processor, microprocessor, generic devices 11, 14, and/or uniquely tailored devices 11, 14 in the environment 10. Those skilled in the art will appreciate that the flow charts illustrate the structures and events of the subject technology, sometimes as computer program code elements, including logic circuits on an integrated circuit, that function according to the inventive technology. As such, the present technology may be practiced by a machine component that renders the program code elements in a form that instructs a digital processing apparatus (e.g., computer or hardware device) to perform a sequence of functional steps similar to or corresponding to those shown in the flow charts.

Figure 2:
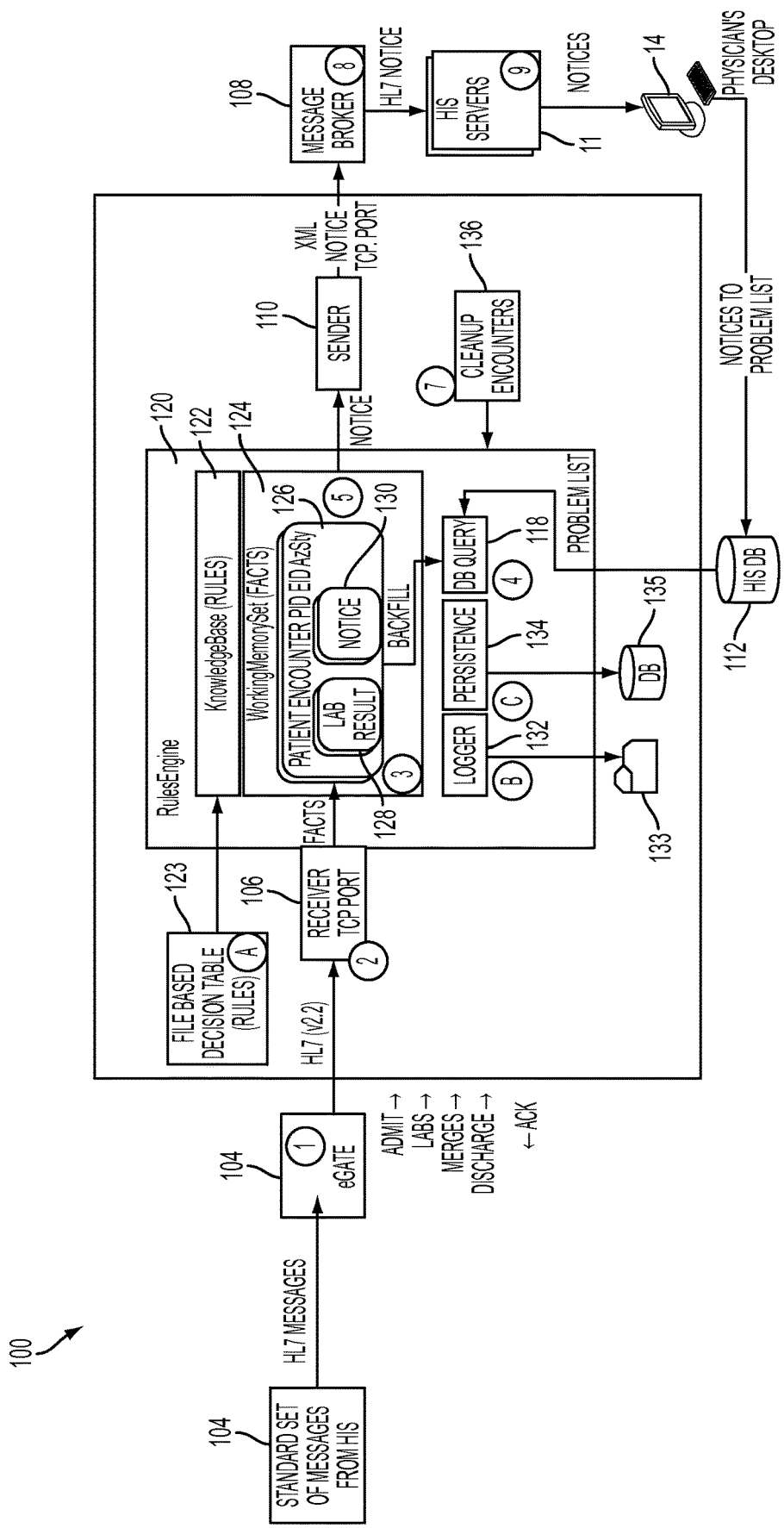
FIG. 2 is exemplary hardware particularly configured to perform a process in accordance with the subject technology.

Referring now to FIG. 2, exemplary hardware is shown particularly configured to perform a process in accordance with the subject technology. The exemplary hardware can be implemented within environment 10 as would be appreciated upon review of the subject disclosure. A healthcare device 100 is present in the environment. The healthcare device 100 may be a single client processing device specially adapted for the purpose or portion of the healthcare device 100 may also be present on other hardware. In any case whether stand-alone or distributed, implementation of the healthcare device 100 may be executed differently based upon constraints such budget, processing, speed, ease-of-use and the like.

Figure 3:
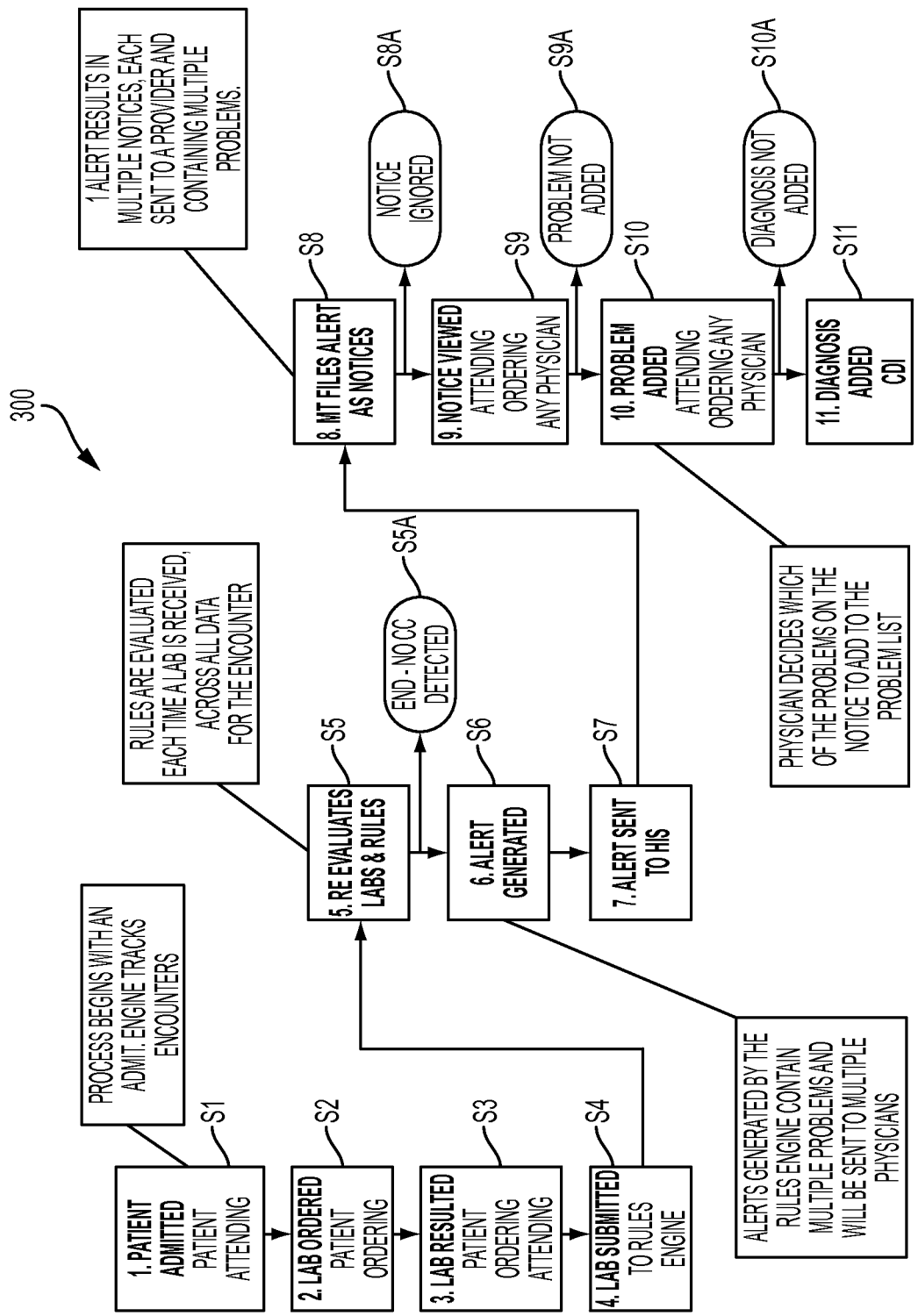
FIGS. 3 and 4 are flowcharts depicting a process in accordance with an embodiment of the present technology.

The healthcare device 100 receives information from a healthcare information system (HIS) 102 (see FIG. 3). The HIS 102 provides a standard set of messages 104 such as admission information, laboratory information, discharge information and the like as described below in more detail with respect to FIGS. 3 and 4. Preferably, the healthcare device 100 has a port 106 in communication with the HIS 102 and provides acknowledgement of the received information.

Still referring to FIG. 2, the healthcare device 100 also provides information to the HIS 102 via a message broker system 108 and HIS servers 11 that ultimately reaches the physician's desktop 14. Preferably, the healthcare device 100 has a sender subsystem 110 in communication with the message broker 108. The information sent to the physician's desktop 14 includes a Problem List among other information like notices for the Problem List that is also stored in the database 112 of the HIS servers 11. The healthcare device 100 also communicates with the HIS database 112 to keep the Problem List up to date via a query subsystem 118.

The healthcare device 100 includes a rules engine 120 that applies knowledge based rules stored in a rules database 122. A file based decision table 123 provides rules related input to the rules database 122. The knowledge based rules are applied to the factual information stored in a facts database 124. The facts database 124 includes all of the patient encounter data 126 such as lab results data 128 and notice data 130. The rules engine 120 also includes a logger module 132 for maintaining files 133 and a persistence module 134 for maintaining a real-time clinical data warehouse database 135 of information as needed. The healthcare device 100 also has a cleanup module 136 for housecleaning tasks and the like.

Although the following example is with respect to co-morbidity, it will be appreciated that the present technology is widely applicable and not limited to this exemplary application. The present technology provides systems, methods and devices that evaluate patient data for potential co-morbidities after each clinical. A clinical may be a lab, BMI, medical order, radiology report, and the like. Alerts are selectively broadcast to targeted users in their existing workflows.

The following non-limiting glossary simply provides a helpful reference for terms commonly used herein.

Alert: A notification sent to selected users when a patient clinical status and details match the clinical triggers and co-morbidity indicators associated to that notification.

Rules Database: The database storing the clinical triggers and co-morbidity indicator combinations organized in business rules.

Clinical Trigger: A set of clinical indicators whose presence in the patients' clinical details initiates an alert. The clinical triggers could be lab results, transfusions, x-rays, etc. The clinical triggers combined with the co-morbidity indicators comprise the business rules behind the alerts.

Co-morbidity Indicator: A condition indicating the potential presence of an undocumented co-morbidity. These are the diagnoses (Dx) related to the patient hospital stay/encounter. The clinical triggers combined with the co-morbidity indicators comprise the business rules behind the alerts.

Alert Process: The process running the clinical triggers and co-morbidity indicators on the patient's clinical data for each hospital stay/encounter and formatting the triggered alerts for further processing.

Encounter Process: The process distinguishing the various patients' hospital stays/encounters.

Encounter Activity Process: The process that tracks the clinical activity during the patient hospital stay/encounter.

CxR: Chest X-Ray.

EF: Ejection Fraction.

Hospital stay/Encounter: A period of time the patient spends in the hospital. It begins with the patient's admission date and ends with the patient's discharge date. One hospital stay=one encounter=one electronic identifier (EID).

Figure 4:
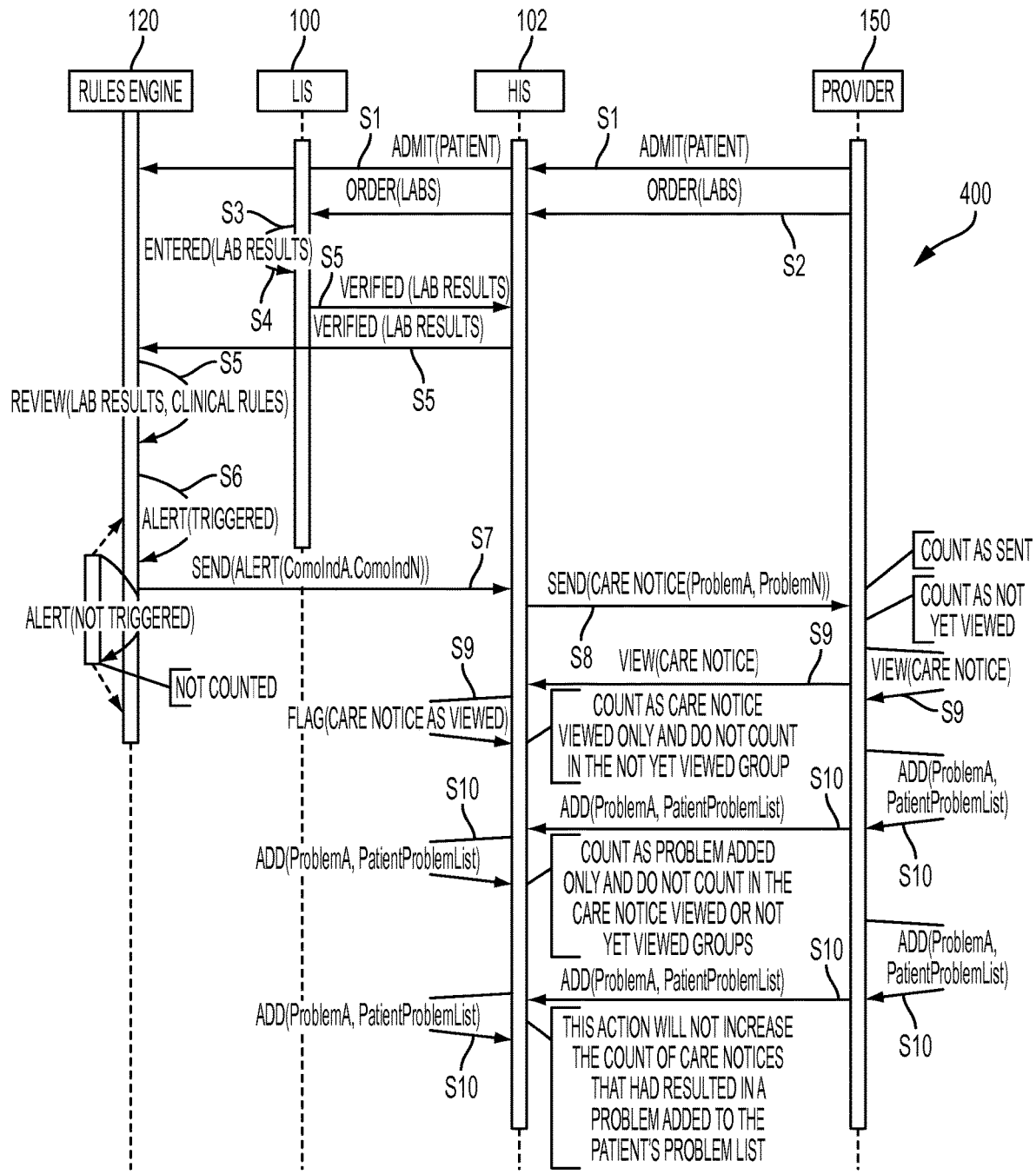

Referring now to FIGS. 3 and 4, there are illustrated flowcharts 300, 400 depicting a process in accordance with an embodiment of the present technology. In a preferred embodiment, an entity (not shown) such as a company, hospital, or clinic hosts a Web site and provide devices 11, 14 to users. The process spans from patient admission to discharge.

At step S1, the patient is admitted by a provider 150 such as a hospital. The provider 150 gathers patient information and the diagnosis by clinicians begins. The patient data is sent to the HIS 102, the healthcare device 100, and the rules engine 120 so that the rules engine 120 can track the encounter. Upon diagnosis, laboratory tests are ordered by the provider 150 as needed at step S2. Again, the HIS 102 and healthcare device 100 receive the data relevant to the lab tests. At step S3, the results of the laboratory tests are distributed throughout the environment 10.

At step S4, the lab results are submitted to the rules engine 120 of the healthcare device 100 for analysis. At step S5, the lab results are verified by the rules engine 120. As commonly occurs, multiple lab results stream in so that the rules engine 120 applies the rules each time a lab results is received for every patient encounter. If no "CC" is detected, the process 300, 400 ends at step S5A.

At step S6, if a rule has been violated, the rules engine 120 generates an alert. At step S7, the alert is sent from the rules engine 120 to the HIS 102. At step S8, multiple notices are generated based on the alert. The status of the notices, such as sent, read, not yet viewed, is tracked in the process 300, 400. If a clinician affirmatively decides to ignore a notice, the activity of the notice being ignored is noted at step S8A.

The notice is viewed at step S9 by clinicians (e.g., the attending physician, the ordering physician, and other caregivers etc.). The viewing of the notice is tracked by the healthcare device 100. If all is in order, the clinician does not take further action in the process 300, 400 at step S9A. However, if the clinician sees a problem, at step S10, the clinician can add a problem that is stored in the healthcare device 100. Similarly, upon review of the problems, the clinician and/or healthcare device 100 can add a diagnosis at step 11 and circulate the information related to the additional diagnosis. If an additional diagnosis is not added, the process 300, 400 stops at step S10A.

As can be seen from FIGS. 1-4, whenever a lab value, medication order, or similar clinical data element is entered into the HIS 102, the new values pass through to the rules engine 120, which is designed specifically to search for all qualifying probable diagnosis codes. Any and all potential diagnosis codes that should be reviewed by the patient's physician are sent to the HIS 102 and appear on the physician's notification list in the HIS 102. The physician is alerted the next time she signs onto the HIS 102 that new items have been added to their notification list. The physician can review the proposed possible diagnosis codes and easily add them to the patient's record by clicking an "Add" button. The assessment rules engine 120 and healthcare device 100 are highly customizable and can be configured to only pass predetermined diagnosis code recommendations and can also control the frequency with which physicians are alerted to new Problem List items. Coding recommendation rules and alert frequencies can be determined by healthcare administrators.

Some of the advantages of the subject technology are: implementing rules based on discrete data (e.g., lab values, med orders, etc.) in near real time; alerting physicians with notices delivered in the HIS 102; moving problems from alert to a Problem List; avoiding repeat alerts for the same co-morbidity; limiting the number of alerts per patient on a periodic basis; adjusting or even turning off rules; screening alerts against the Problem List; and tracking notices dismissed without being added to the Problem List. Upon implementation within a healthcare office or hospital, the healthcare device 100 improves patient safety by ensuring all appropriate co-morbidity diagnosis codes are filed on patient records, and healthcare cost reimbursement will be increased significantly. For example, incorrect coding on renal failure versus acute renal failure could result in a reimbursement difference of tens of thousands of dollars on a single patient visit.

Figure 5:
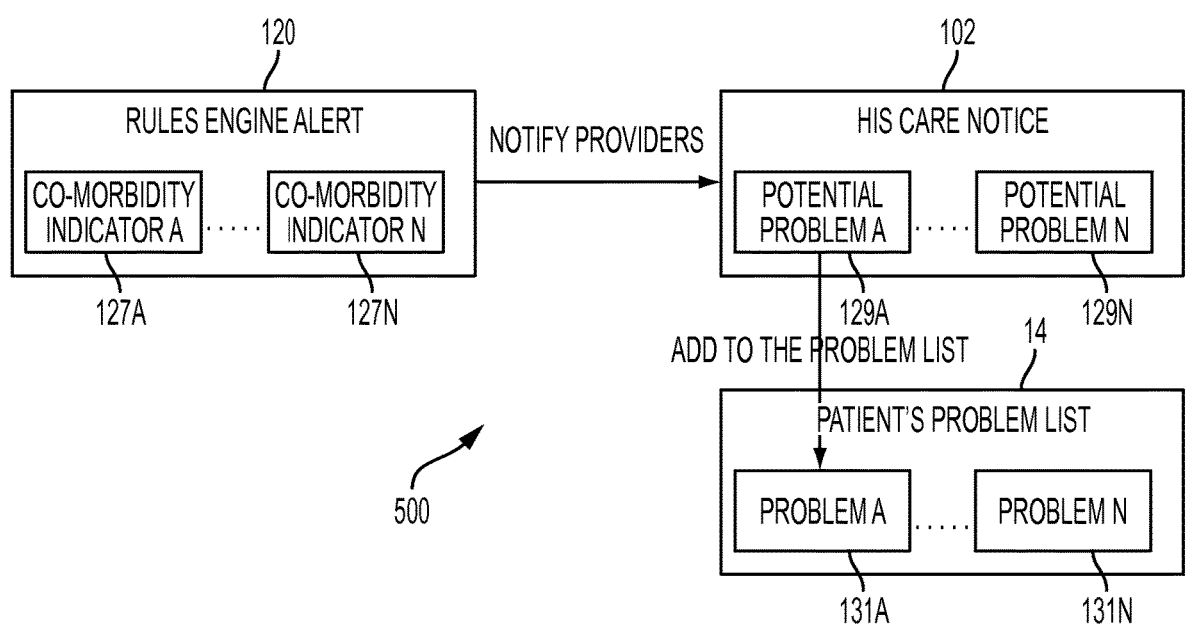
FIGS. 5 and 6 are informational flow diagrams in accordance with an embodiment of the present technology.
Figure 6:
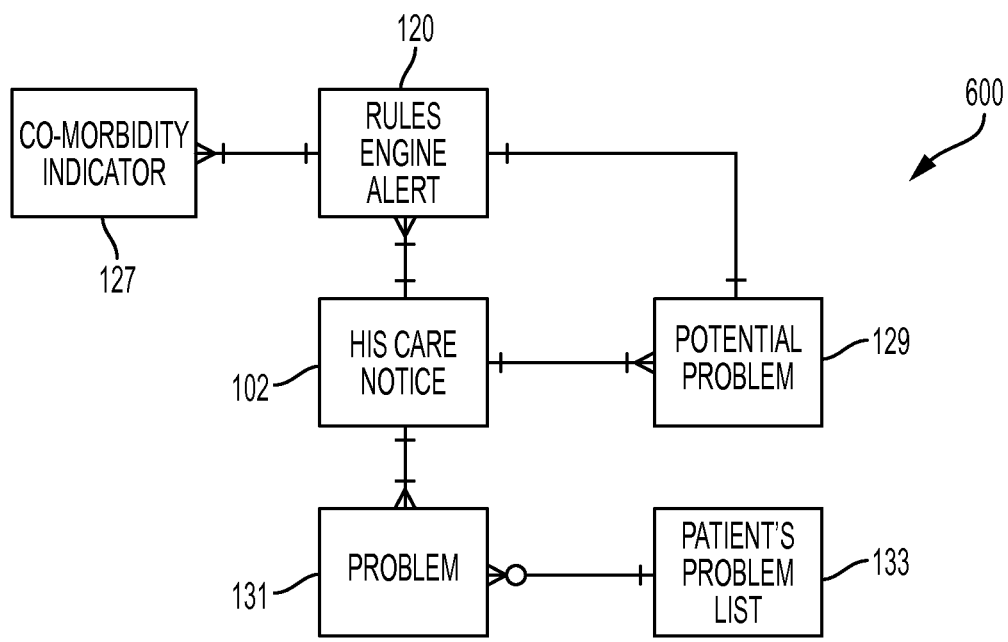

Referring now to FIGS. 5 and 6, informational flow diagrams 500, 600 are shown. The flow diagrams 500, 600 illustrate one way in which information passes throughout the environment 10. In particular, when the rules engine 120 of the healthcare device 100 sees a plurality of co-morbidity indicators 127A-N, the rules engine 120 notifies the providers via the HIS 102. The HIS 102 generates and stores a plurality of potential problem notices 129A-N corresponding to the co-morbidity indicators 127A-N. The HIS 102 adds the potential problem notices 129A-N to the patient's Problem List 133 that eventually is presented to the clinician at the physician's desktop 14 as a plurality of problems 131A-N on the patient's Problem List 133.

Figure 7:
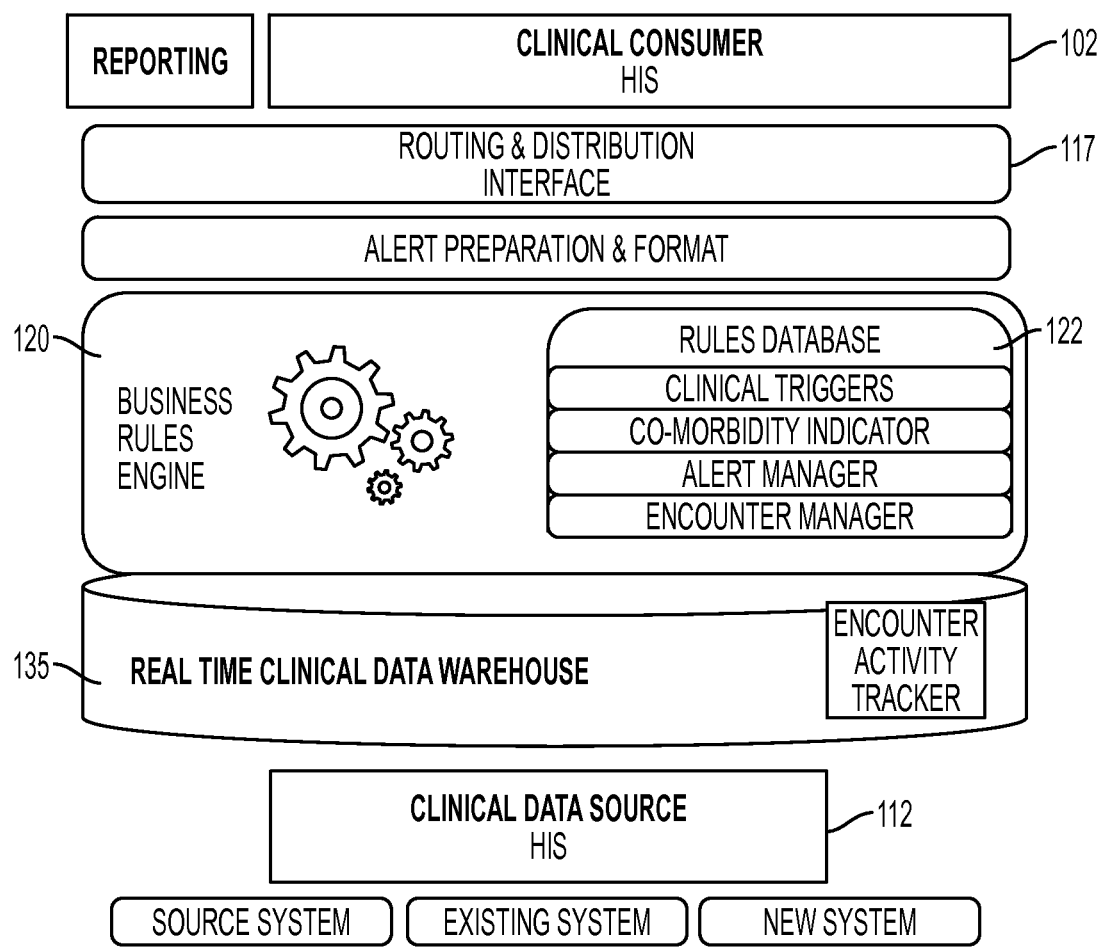
FIG. 7 is a somewhat schematic diagram of another arrangement for the subject technology in accordance with an embodiment of the present technology.

Referring now to FIG. 7, a somewhat schematic diagram of another arrangement for the subject technology is shown. The schematic of FIG. 7 illustrates a way in which the techniques herein add to currently existing systems (e.g., Real Time Clinical Data Warehouse 112, a HIS 102, a Middleware eGate, Message Broker interface 117, etc.). It is envisioned that interfaces are developed to accommodate the functionality described herein. The HIS 102 generates the necessary data, such as labs, med orders, radiology, pathology, etc. Note that certain information, such as radiology and pathology, may require natural language processing, or "NLP". In one embodiment, an encounter level "registry" of activity is updated in real time that is illustratively the central point to anchor rules searches. The encounter level "registry" could be part of the Real-Time Clinical Data Warehouse 112. Also, data can feed from many sources such as the HIS 102 or other components of the Real Time Clinical Data Warehouse 112, third parties and the like.

In one embodiment, the rules engine 120 sift through the Real Time Clinical Data and trigger alerts. Rules may include triggers (e.g., a lab result outside of a given range). Triggers combine to form rules (e.g., a lab result outside a range AND a procedure performed). Alerts are managed based on facility, user, presence of other indicators, and the like. Alerts may be tracked per encounter. Note that the Alert text can be formatted for interface to any number of systems, including the HIS 102 (e.g., taking advantage of source systems normal notification features).

Example alerts may include such text as: "This patient has hyperglycemia with widened Anion Gap consistent with DKA."; "This patient has a Creatinine greater than 1.5 or an increase of greater than 0.5 mg/dl since last test"; and "This patient has Hypoxemia or a Respiratory Acidosis with pCO2 greater than 50 mmHg." Also, various other text/indicators may be included, such as "This alert has been automatically generated from pre-set laboratory thresholds", or "A clinical correlation is required".

Any number of rules may be created based on healthcare standards, from which the co-morbidity assessment rules engine 120 may make the corresponding assessments. For example, the table shown in FIG. 8 lists a small subset of rules, and their corresponding entry values. Illustratively, a certain code may correspond to a particular diagnosis description (e.g., hyposmolality), which is based on one or more clinical triggers (e.g., sodium <130). Other data may also be stored, such as whether to store this information upon discharge from the medical facility, a translated code for a healthcare information system, various priorities and statuses of the codes, alert trigger filters (e.g., another trigger supersedes this one), various diagnoses codes that should prevent a given alert from triggering if they are present on the patient's Problem List in the healthcare information system, and other codes for which the particular diagnosis may be bundled with (e.g., that need to be assessed further based on their typical medical correlation).

Regarding the business rules herein, alerts and notices are be sent to the physicians as close to real time as possible. Also, both the Attending and Ordering Physicians should be notified at the same time. Note that the techniques herein may be generally configured to avoid alert fatigue, such as by avoiding repeat alerts for the same clinical condition. For example, repeat alerts for the same clinical condition should be avoided. In other words, if during the Inpatient stay a clinical rule is triggered multiple times based on the patient's clinical data, the corresponding physicians would be notified only once (i.e., the first time).

Also, the techniques may limit to one alert per hospitalization/encounter/patient visit, where that one alert may combine multiple Clinical Rule Alerts that triggered from the patient's clinical data. In one embodiment, alerts will not be sent after the patient has been discharged. Also, if multiple clinical rules trigger together, the preferred delivery is one notice with all potential diagnosis as separate diagnoses to be added to the healthcare information system Problem List. For instance, if there are three problems per patient (e.g., different rules generated unrelated comorbidities at roughly the same time, for example, from the same panel of results), the Alerts will appear in the management system as one notice for the patient. Also, if multiple clinical rules that sharing the same clinical triggers trigger together, the generated Alerts will be delivered in one bundled notice.

Alerts may also be triggered depending on the way the physicians react to the notices in the HIS 102. For instance, if in the HIS 102 the physician adds the diagnosis from the notice to the patient's Problem List, the alert should not fire the next time when its clinical trigger suggests. Also, if in the HIS 102, the physician acknowledges the notice but does not add the diagnosis from the notice to the patient's Problem List, the alert should not fire the next time when its clinical trigger suggests. Further, if in the HIS 102, the physician ignores the notice, the alert should fire again the next time when its schedule suggests. Notably, in one specific embodiment, once an alert or notice message is sent to the HIS 102, it is not be possible to recall the alert or notice message.

Also, a lag time may be built in to account for lab processing when multiple labs are ordered at the same time. In one embodiment, alerts may be linked to a certain day of the patient's LOS (e.g., determined on a rule by rule basis). Further, when the clinical triggers for a rule consist of multiple labs/mnemonics, for example Glucose and Anion Gap, then only labs that are no more than six hours between may be considered. For example, the six-hour consideration comes into play when simple tests on multiple lab results come in at different times.

For example, the diabetes rule may be as follows: GLUTEST>300 AND AGAPTEST>12. Assuming the following scenario: 00:00 hours: GLUTEST=200, AGAPTEST=15; Does not trigger because GLUTEST<=300; 07:00 hours: GLUTEST=400, AGAPTEST=10; Does not trigger because even though GLUTEST is now >300, the previous AGAPTEST=15 that could have triggered the rule is now more than six hours old; 08:00 hours: GLUTEST=200, AGAPTEST=14; and Triggers because AGAPTEST is now >12, and even though the current GLUTEST<=300, the previous GLUTEST=400 does match the rule and is not more than six hours old. It could be that if the GLUTEST and AGAPTEST results come together, then the earlier result should be disregarded. However, it is preferable that the rules are constructed or interpreted in this manner. The earlier GLUTEST result will be considered. Note that this six-hour rule should not be applied for the temporal conditions when looking at the first lab since admission, or the oldest lab in the last 36 hours, for example.

In one embodiment, clinical rules may be divided into high and low volume groups. If so, following the requirement to send as few alerts as possible, these two groups of alerts may be scheduled as follows: (i) The High Volume Clinical Rule Alerts would be sent to the physicians once per shift, preferably around each shift start time based on the data analysis of the labs drawn, labs final result in the healthcare information system, physician schedules, and the best time for such notification (e.g., 8:30 am)); and (ii) The Low Volume Clinical Rule Alerts would be sent as the Low Volume Clinical Rule Alerts occur.

Figure 9:
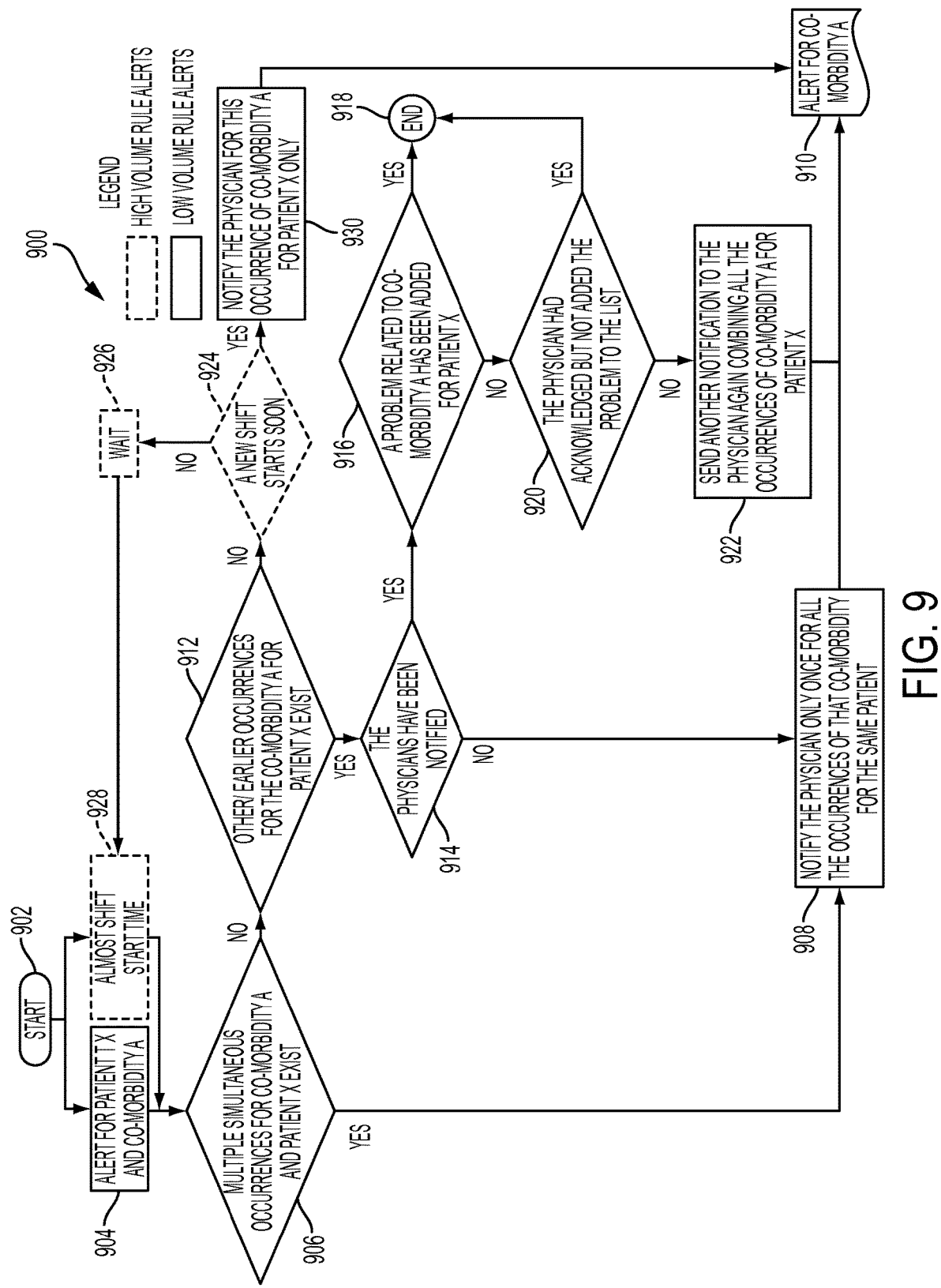
FIG. 9 illustrates a data flow process in with High Volume and Low Volume Clinical Rule Alerts in accordance with an embodiment of the present technology.

FIG. 9 illustrates data flow or process 900 in with High Volume and Low Volume Clinical Rule Alerts in more detail to illustrate whom to notify, various embodiments and configurations. The process 900 starts at step 902. In brief overview, the Attending and Ordering physicians, as recorded in the rule definition file, were notified all the time. However, if the attending provider in the HIS 102 is not the correct one, problems may arise. As such, the techniques herein may determine the provider to send notice to from a patient audit log. That is, in an effort to correctly identify the provider currently caring for the patient, the techniques may not send the notice to the Attending and Ordering Provider as the primary destination, but rather will search the patient audit log for the patient account generating the notice to determine the most recent two providers to access that record within the past X hours (e.g., 8 hours). If these providers can be determined, the techniques will send the notice to those providers. If only one provider can be determined, the techniques will only send the notice to that provider. If no provider can be determined, the techniques will send the notice to the Ordering and Attending Providers. In order to bundle notices according to the techniques herein, as mentioned above, the rightmost column of the table of FIG. 8 has all codes that share the clinical triggers on that line.

At step 904, the process 900 evaluates if there are multiple simultaneous occurrences for co-morbidity A and patient X. If yes, the process 900 proceeds to step 908 to notify the physician only once for all the occurrences by sending an alert at step 910. If there are not multiple simultaneous occurrences for co-morbidity A and patient X at step 906, the process 900 proceeds to step 912. At step 912, if other earlier occurrences of co-morbidity A for patient X exist, the process 900 proceeds to step 914 to determine if the physician has been notified. If the physician has not been notified, the process 900 flows to step 908 to generate an Alert as described above.

If the physician has been notified at step 914, the process 900 flows to step 916 to evaluate if a problem related to co-morbidity A has been added to patient X. If a problem related to co-morbidity A has been added to patient X, the process 900 proceeds to end at step 918. However, at step 916, if a problem related to co-morbidity A has not been added to patient X, the process 900 proceeds to step 920 to evaluate whether or not the physician has acknowledged but not added the problem to the list. If the physician has added the problem to the list, the process 900 again ends at step 918. At step 920, if the physician has not added the problem to the list, the process 900 proceeds to step 922 to send another notification to the physician combining all occurrences of co-morbidity A for patient X and an Alert is sent at step 910.

Still referring to FIG. 9, at step 912, if other earlier occurrences of co-morbidity A for patient X do not exist, the process 900 proceeds to step 924 to evaluate if a new shift starts soon. If the new shift is not about to start, the process 900 flows to step 926 to wait out a predetermined delay. After the delay, the process 900 flows to step 928 so that the process 900 returns to step 906 at approximately the same time that the new shift starts. At step 924, if a new shift starts soon, the process 900 proceeds to step 930 to notify the physician for the occurrence of co-morbidity A for patient X and send an Alert for the same at step 910.

In one embodiment, the rules engine 120 may resend a notice under certain conditions. The timing between the notices should be set (e.g., 30 minutes) and may be counted from the time the rules engine 120 receives the lab for the first notice. This could be done by using the time the rules engine 120 sends the notice based on the lab received instead as processing speed is high and the difference between the two timestamps would be negligible. As a result, before the rules engine 120 sends a notice, the rules engine 120 looks back and considers whether the latest notice sent for that code was sent more than 30 minutes ago and what was the provider reaction to it in the HIS 102.

Generally, when multiple notices have been sent, preferably, the physician only needs to look at the latest one. To illustrate the details for the logic here, assume a scenario where a first notice is sent when lab results match certain clinical triggers and a notice is sent out. The physician flags it in the healthcare information system as status="Do Not Add" and selects the reason as "Insufficient Data" (ID) or "Unreliable Specimen" (CUS). Subsequently, if another lab comes in 30 minutes or later that matches the same clinical triggers, a new notice should be sent based on the latest lab results. On the other hand, if another lab comes in prior to the 30-minute deadline that matches the same clinical triggers, a new notice should not be sent.

Figure 11:
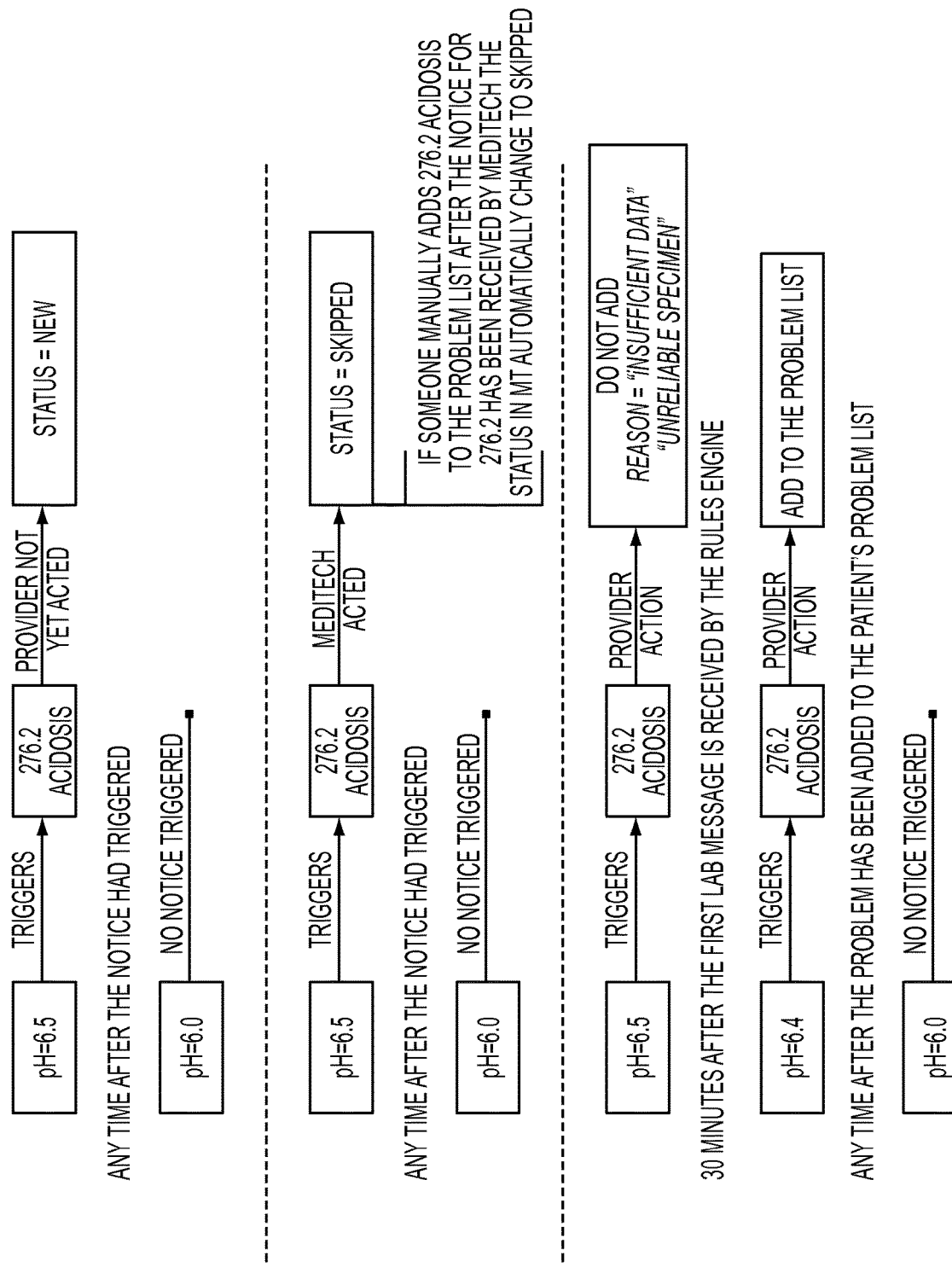

Referring now to FIGS. 10-12, various examples of notice triggering according to the subject technology are illustrated. As would be appreciated based upon review of the subject disclosure, the subject technology may also assist in the processing of medications. For instance, the physicians may use the HIS 102 to order labs (ORU), pharmacy (RDE) or radiology (ITS). In this event, the pharmacy part of the order is verified by a pharmacist before leaving the HIS 102 via a system such as eGate. When a pharmacy order is placed, an interface may allow the system to know if it has been fulfilled and/or given to the patient.

According to one or more embodiments herein, the rules engine 120 of the healthcare device 100 may take into account various mnemonic normalization. In particular, a translation is made ("from" and "to"), where there could be many "From" columns (e.g., many different mnemonics used) and only one "To" column (e.g., a single system-based term). For example, "From" terms may include {GLU.2, GLU., GLU, FBS, WGLUC, FBSL, FBS.2} and the "To" term for the system (i.e., translating all of the "From" terms) could be {GLUTEST}. Others, such as from {PHBG, PHBG2, PHABG, PHBGM, PHBGV} to {PHTEST}, and so on, may be configured. Those skilled in the art will appreciate that these are merely examples, and any translations may occur if so configured.

Since the rules are generally based on medical practice, the rules may be added or changed over time. For example, the creation of new clinical and business (physician and patient) rules may be handled as a collection of data mapping and analysis between advisory panels of medical experts, and may require test data sets to ensure adequate processing. For clinical rule creation, the co-morbidity diagnosis and related clinical triggers may be identified (Co-morbidity Dx+Clinical Trigger(s)=Clinical Rule Definition), and the data source for the clinical triggers may also be identified (e.g., integration analyst research, the healthcare information system analyst verification, clinical verification, etc.).

In one embodiment, accuracy of the healthcare device 100 is constantly monitored and tuned based on a problem distributions dashboard (not shown). The problem distributions dashboard displays a summary of provider actions for each rule. For example, the summary includes the percentage of times providers accepted the suggested problem diagnosis and their comments if the provider indicated an alternate diagnosis. The problem distributions dashboard allows reviewing each rule to observe how effective the rule is at suggesting problems that providers add and identifying rules where providers are rejecting problems or suggesting alternatives that can be incorporated into the healthcare device 100. Preferably, the monitoring and tuning occurs after Step S11 in FIG. 3 but such monitoring and tuning may occur throughout the process 300.

The healthcare device 100 also includes a resources recognized dashboard (not shown). The resources recognized dashboard combines abstracting data (e.g., final DRG) obtained after discharge with notices added during the patient's visit to calculate an approximate value of resources recognized due to the healthcare device 100. Based on the final DRG, it is possible to identify patients for whom a healthcare device notice was sent, a problem was added, and a final DRG calculated that includes a co-morbidity or multiple co-morbidities. Preferably, the calculations of the resources recognized dashboard occurs after Step S11 in FIG. 3 but such may occur throughout the process 300.

Additional electronic dashboards may be used to monitor other operational aspects of the healthcare device 100. The dashboards may monitor overalerting (e.g., monitor the number of alerts per patient), notices statistics (e.g., monitor deployment and adoption of the healthcare device 100 across hospitals and type of hospitalists), actions by provider (e.g., evolved into Problem Distributions) and CMI Trend (e.g., monitoring impact of rules and problems included in the healthcare device 100 with respect to impact on influencing the final DRG).

Illustratively, the techniques described herein may be performed by hardware, software, firmware, or any combination thereof. In particular, software program instructions directed to the co-morbidity assessment rules engine 120 herein may be stored in a memory and executed by a processor on a corresponding computing device. Also, various interfaces may allow the program to communicate with other programs, such as APIs, or more specific protocol interfaces, such as HL7 Interfaces (HL7 is a common framework and standards for the exchange, integration, sharing, and retrieval of electronic health information), etc.

The foregoing description of preferred embodiments of the present technology has been presented for the purposes of illustration and description. It is not intended to be exhaustive or to limit the technology to the precise form disclosed. Modifications and variations are possible in light of the above teachings, or may be acquired from practice of the technology. The embodiments were chosen and described in order to explain the principles of the technology and its practical application to enable one skilled in the art to utilize the technology in various embodiments and with various modifications as are suited to the particular use contemplated.

What is claimed is:

1. An integrated healthcare device with embedded co-morbidity assessment functionality, the healthcare device comprising:
    a message broker hardware module configured to relay information generated by the integrated healthcare device to one or more user devices;
    an input port communicatively coupled to a Healthcare Information System (HIS) and configured to receive patient's information from the HIS; and
    a rules engine hardware module configured to apply a plurality of co-morbidity assessment rules to the patient's information received from the HIS via the input port to determine if at least one clinical trigger is present and is further configured to determine a diagnosis based on the received patient's information and presence of a determined clinical trigger, the rules engine hardware module further comprising:
    a co-morbidity manager hardware module configured to maintain a plurality of co-morbidity indicators; and
    an alert manager hardware module configured to:
        send a first alert, using the message broker, to a selected user associated with the patient in response to determining that the at least one clinical trigger is present;
        determine when multiple clinical triggers are triggered together for a plurality of comorbidities from common patient results in the patient's information received from the HIS;
        responsive to determining multiple clinical triggers are triggered together for a plurality of comborbidities, an alert for each unrelated comorbidity is bundled together with other alerts for the other unrelated comorbidities in the same first alert whereby an alert is triggered dependent upon a way a physician reacted to a previous notice in the HIS;
        track status of the first alert; and
        selectively present predetermined diagnosis code recommendations to a physician to enable addition of a predetermined diagnosis code to a patient record.

2. The integrated healthcare device of claim 1, wherein the received patient's information comprises patient's laboratory test results.

3. The integrated healthcare device of claim 1, wherein the rules engine hardware module is further configured to crosswalk the diagnosis into medical coding information for reimbursement purposes, wherein the selected user is a healthcare provider.

4. The integrated healthcare device of claim 1 further comprising a problem distributions dashboard hardware module configured to display a summary of user actions for each one of the plurality of co-morbidity assessment rules.

5. The integrated healthcare device of claim 4, wherein the summary includes an indicator of how effective each co-morbidity assessment rule is at suggesting problems that users add.

6. The integrated healthcare device of claim 1, wherein sending of the first alert is contingent upon a recipient physician's shift time.

7. The integrated healthcare device of claim 1, wherein the alert manager is further configured to determine if the first alert has been previously sent to the physician for the same co-morbidity to cancel the sending of the first alert if determined a previous alert was sent for same co-morbidity.

* * * * *